(12) United States Patent
Edmondson, III et al.

(10) Patent No.: US 10,950,350 B2
(45) Date of Patent: Mar. 16, 2021

(54) SKILLED NURSING FACILITY PATIENT TRIAGE SYSTEM

(71) Applicant: KONINKLIJKE PHILIPS N.V., Eindhoven (NL)

(72) Inventors: Thomas Lee Edmondson, III, Baltimore, MD (US); Bridgette Leonard, Framingham, MA (US); Karsten Anthony Alexander Russell-Wood, Baltimore, MD (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 144 days.

(21) Appl. No.: 15/781,171

(22) PCT Filed: Dec. 6, 2016

(86) PCT No.: PCT/EP2016/079962
§ 371 (c)(1),
(2) Date: Jun. 4, 2018

(87) PCT Pub. No.: WO2017/097789
PCT Pub. Date: Jun. 15, 2017

(65) Prior Publication Data
US 2018/0358126 A1 Dec. 13, 2018

Related U.S. Application Data

(60) Provisional application No. 62/263,953, filed on Dec. 7, 2015, provisional application No. 62/369,813, filed on Aug. 2, 2016.

(51) Int. Cl.
*G16H 50/30* (2018.01)
*G16H 10/60* (2018.01)
(Continued)

(52) U.S. Cl.
CPC ............ *G16H 50/30* (2018.01); *G16H 10/60* (2018.01); *G16H 40/20* (2018.01); *G16H 40/40* (2018.01); *G16H 40/60* (2018.01); *G16H 40/67* (2018.01)

(58) Field of Classification Search
CPC ........ G16H 40/20; G16H 50/30; G16H 10/60; G16H 50/20
(Continued)

(56) References Cited

U.S. PATENT DOCUMENTS 7,315,825 B2   1/2008   Rosenfeld et al.
8,998,830 B2   4/2015   Halperin et al.
(Continued)

OTHER PUBLICATIONS

Gage, B. et al., "Examining Post Acute Care Relationships in an Integrated Hospital System", Prepared for Susan Bogasky, Assistant Secretary for Planning and Evaluation (ASPE), U.S. Department of Health and Human Services, Feb. 2009.
(Continued)

*Primary Examiner* — Hiep V Nguyen

(57) ABSTRACT

The present disclosure pertains to a system for facilitating computer-assisted care for patients, including, for example, skilled nursing facility (SNF) patients at risk of clinical deterioration and/or in need of medical intervention relative to a larger SNF patient population. In some embodiments, the system determines care information scores for SNF patients using a first set of severity weights associated with individual components of the care information. The system determines SNF enhancement scores for the individual patients using a second set of severity weights associated with individual components of collected SNF enhancement information, wherein the second set of severity weights are heavier than the first set of severity weights such that the enhancement scores are weighted more heavily than the care information scores. The system combines the care information scores with the enhancement scores for patients to determine a combined score indicating risk of clinical deterioration and/or need for medical intervention.

18 Claims, 7 Drawing Sheets

(51) Int. Cl.
*G16H 40/40* (2018.01)
*G16H 40/67* (2018.01)
*G16H 40/20* (2018.01)
*G16H 40/60* (2018.01)

(58) Field of Classification Search
USPC .......................................................... 705/3
See application file for complete search history.

(56) References Cited

U.S. PATENT DOCUMENTS

| | | | |
|---|---|---|---|
| 2004/0103001 A1 | 5/2004 | Mazar et al. | |
| 2009/0093686 A1* | 4/2009 | Hu | G06F 19/00 600/300 |
| 2010/0100392 A1* | 4/2010 | Rothman | G06Q 50/22 705/2 |
| 2011/0077968 A1* | 3/2011 | Kelly | G16H 50/20 705/3 |
| 2012/0004925 A1 | 1/2012 | Braverman et al. | |
| 2013/0249695 A1 | 9/2013 | Hann | |
| 2013/0346105 A1 | 12/2013 | Ryan et al. | |
| 2015/0213225 A1 | 7/2015 | Amarasingham et al. | |

OTHER PUBLICATIONS

Mor, V. et al., "The Revolving Door of Rehospitalization from Skilled Nursing Facilities", Health Affairs 29, No. 1, 2010, 57-65.

Perry, M. et al., "To Hospitalize or Not to Hospitalize? Medical Care for Long-Term Care Facility Residents", Kaiser Foundation, Oct. 2010.

Ouslander, J. et al., "The INTERACT Quality Improvement Program: An Overview for Medical Directors and Primary Care Clinicians in Long-Term Care", J Am Med Dir Assoc., Mar. 2014.

Jiang, Y. et al., "Using mobile health technology to deliver decision support for self-monitoring after lung transplantation", Int J Med Inform., Oct. 2016.

Gifford, D., "Nursing Homes Are the Solution on Readmissions", https://www.healthaffairs.org/do/10.1377/nblog20140117.036346/full/, Jan. 17, 2014.

"Collaborative Charter: Reducing Readmissions by Improving Transitions in Care", Institute for Healthcare Improvement, 2009.

"Rehospitalization from Skilled Nursing Facilities: Implications for Policy", Robert Wood Johnson Foundation Findings Brief, vol. XII, No. 9, Feb. 2010.

Wolfe W, "What health care reform is all about", Minneapolis Star Tribune, Jul. 14, 2009.

McGillion, M. et al., "Technology-Enabled Remote Monitoring and Self-Management—Vision for Patient Empowerment Following Cardiac and Vascular Surgery: User Testing and Randomized Controlled Trial Protocol", JMIR Research Protocols, vol. 5, issue 3, Aug. 1, 2016.

\* cited by examiner

ABSTRACT# SKILLED NURSING FACILITY PATIENT TRIAGE SYSTEM

CROSS-REFERENCE TO PRIOR APPLICATIONS

This application claims the benefit or priority of Provisional Application 62/263,953 filed Dec. 7, 2015 which is incorporated herein in whole by reference.

BACKGROUND

1. Field

The present disclosure pertains to a system and method for facilitating computer-assisted care for skilled nursing facility (SNF) patients, including, for example, SNF patients at risk of clinical deterioration and/or in need of medical intervention relative to a larger population of SNF patients.

2. Description of the Related Art

In the U.S., millions of residents rely on skilled nursing facilities. Of all potentially avoidable hospitalizations, nearly half of such cases originate from a skilled nursing facility. Although computer-assisted care systems exist in some form, such systems are not tailored for SNF patients. Treating a resident SNF population is typically more complex than treating a general population of patients because the SNF population of patients is typically older, frail, disabled, and/or medically ill. Also unique to the SNF setting is an extensive set of federal and state regulations that lead to fragmented documentation of treatments for individual SNF patients. At the individual patient level, clinicians must capture and consider multiple data elements related to their patients' diseases, but the presentation of disease is altered in this frail population, making diagnosis and management more challenging than in less sick populations.

SUMMARY

Accordingly, one or more aspects of the present disclosure relate to a system configured to facilitate computer-assisted care for skilled nursing facility (SNF) patients at risk of clinical deterioration and/or in need of medical intervention relative to a larger population of SNF patients. The system comprises one or more hardware processors, one or more computing systems, and/or other components. The one or more hardware processors are configured by machine-readable instructions to: obtain care information for the larger population of SNF patients, the care information comprising physiological information (e.g., including information conveyed by answers to survey questions, information collected from one or more medical devices used to monitor and/or treat SNF patients, information in medical records databases associated with SNF patients, and/or other information) collected by caregivers during care for the larger population of SNF patients; facilitate collection of SNF enhancement information for the larger population of SNF patients, the SNF enhancement information comprising information related to SNF specific care provided to the larger population of SNF patients; determine care information scores for individual SNF patients based on the obtained care information, the care information scores determined using a first set of severity weights associated with individual components of the care information; determine SNF enhancement scores for the individual SNF patients based on the SNF enhancement information, the SNF enhancement scores determined using a second set of severity weights associated with individual components of the SNF enhancement information, wherein the second set of severity weights are heavier than the first set of severity weights such that the SNF enhancement scores are weighted more heavily than the care information scores for the individual SNF patients; and combine the care information scores with the SNF enhancement scores for the individual SNF patients to determine a combined score that indicates risk of clinical deterioration and/or a need for medical intervention for the individual SNF patients. The one or more computing devices are configured to display the combined scores for the individual SNF patients as a triaged list of individual SNF patients in a view of a graphical user interface displayed on the one or more computing devices.

Yet another aspect of the present disclosure relates to a method for facilitating computer-assisted care for skilled nursing facility (SNF) patients at risk of clinical deterioration and/or in need of medical intervention relative to a larger population of SNF patients with a display system. The system comprises one or more hardware processors, one or more computing devices, and/or other components. The method comprises: obtaining, with the one or more hardware processors, care information for the larger population of SNF patients, the care information comprising physiological information collected by caregivers during care for the larger population of SNF patients; facilitating, with the one or more hardware processors, collection of SNF enhancement information for the larger population of SNF patients, the SNF enhancement information comprising information related to SNF specific care provided to the larger population of SNF patients; determining, with the one or more hardware processors, care information scores for individual SNF patients based on the obtained care information, the care information scores determined using a first set of severity weights associated with individual components of the care information; determining, with the one or more hardware processors, SNF enhancement scores for the individual SNF patients based on the SNF enhancement information, the SNF enhancement scores determined using a second set of severity weights associated with individual components of the SNF enhancement information, wherein the second set of severity weights are heavier than the first set of severity weights such that the SNF enhancement scores are weighted more heavily than the care information scores for the individual SNF patients; combining, with the one or more hardware processors, the care information scores with the SNF enhancement scores for the individual SNF patients to determine a combined score that indicates risk of clinical deterioration and/or a need for medical intervention for the individual SNF patients; and displaying, with the one or more computing devices, the combined scores for the individual SNF patients as a triaged list of individual SNF patients in a view of a graphical user interface displayed on the one or more computing devices.

Still another aspect of present disclosure relates to a system for computer-assisted care for skilled nursing facility (SNF) patients at risk of clinical deterioration and/or in need of medical intervention relative to a larger population of SNF patients. The system comprising: means for obtaining care information for the larger population of SNF patients, the care information comprising physiological information collected by caregivers during care for the larger population of SNF patients; means for facilitating collection of SNF enhancement information for the larger population of SNF patients, the SNF enhancement information comprising information related to SNF specific care provided to the larger population of SNF patients; means for determining care information scores for individual SNF patients based on the obtained care information, the care information scores determined using a first set of severity weights associated with individual components of the care information; means for determining SNF enhancement scores for the individual SNF patients based on the SNF enhancement information, the SNF enhancement scores determined using a second set of severity weights associated with individual components of the SNF enhancement information, wherein the second set of severity weights are heavier than the first set of severity weights such that the SNF enhancement scores are weighted more heavily than the care information scores for the individual SNF patients; means for combining the care information scores with the SNF enhancement scores for the individual SNF patients to determine a combined score that indicates risk of clinical deterioration and/or a need for medical intervention for the individual SNF patients; and means for displaying the combined scores for the individual SNF patients as a triaged list of individual SNF patients in a view of a graphical user interface displayed on the means for displaying.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
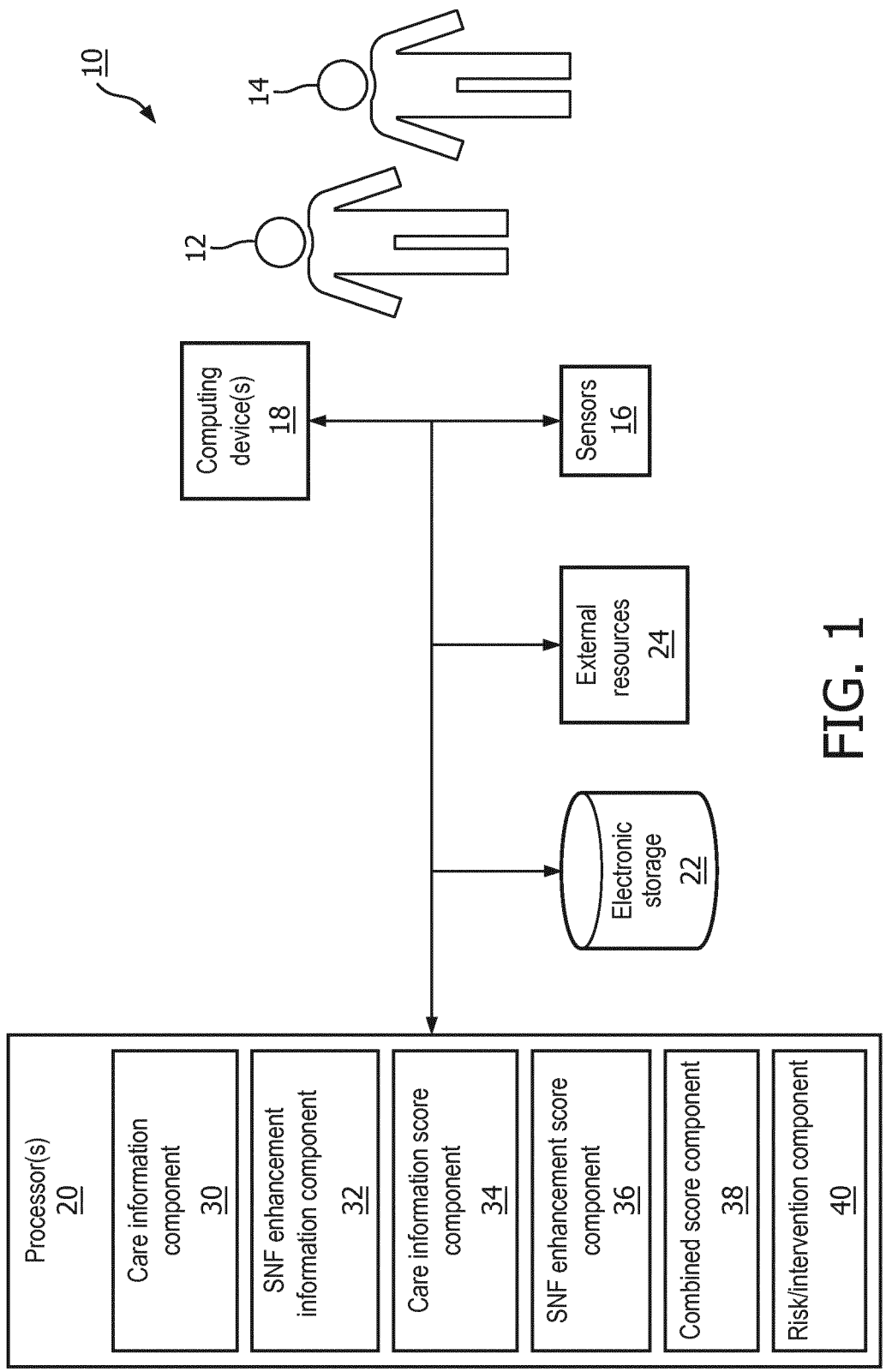
FIG. 1 is a schematic illustration of a system for facilitating computer-assisted care for SNF patients.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 for facilitating computer-assisted care for SNF patients. When assessing the SNF population, caregivers 14 (e.g., clinicians, doctors, nurses, dieticians, physical therapists, central care coordinators, etc.) may improve their diagnostic sensitivity and/or specificity by including an assessment of a patient's functional status and/or overall health status in information they record about a patient 14. As a result of federal and state regulations, a SNF documents a large database of clinical information in flowsheets, with an individual flowsheet being physically stored in a particular location (e.g., at a nurse's station and/or off-site such as within the office of a physical therapist and/or dietitian, etc.). The data in the flow sheets may be invaluable in clinical decision making, but in most circumstances, there is not a review of the data by a treating clinician in a timely fashion and/or in a productive manner. Moreover, routine coordination of this voluminous amount of data is traditionally not done except on very rare occasions during a quality assurance investigation. This inaction may lead to a citation of deficiencies by a state's health department during inspections, delay in diagnosis of a patient 12, delay in recognition of a patient 12 in need of medical care, potentially avoidable hospitalizations, and/or other consequences.

System 10 is configured to, through trending of physiologic observations, measurements, survey responses, and/or other information, provide a caregiver 14 (e.g., clinicians, doctors, nurses, dieticians, physical therapists, central care coordinators, etc.) the opportunity to monitor the health of a population of SNF patients, apply predictive analytics, and identify individual patients 12 who may benefit from additional interventions and/or additional assessment by clinicians. System 10 is configured to recognize changes in the conditions of patients 12 early in the time course of an episode of illness, which may enhance care within a SNF and/or reduce potentially avoidable transfers to the hospital. System 10 is configured to determine a combined score (e.g., based on intervention rules, pattern rules, scoring of measurements, and/or other information which is typically not evaluated by physicians and/or nurses in a timely, proactive fashion) that indicates risk of clinical deterioration and/or a need for medical intervention for the individual SNF patients 12, cause display of elements (e.g., the combined scores, a triaged list of patients 12, colored flag warnings, etc.) based on information unique to the management of patients in the care setting of a SNF on a graphical user interface visible to caregivers 14, and/or perform other activities that enhance care in a SNF.

Figure 2:
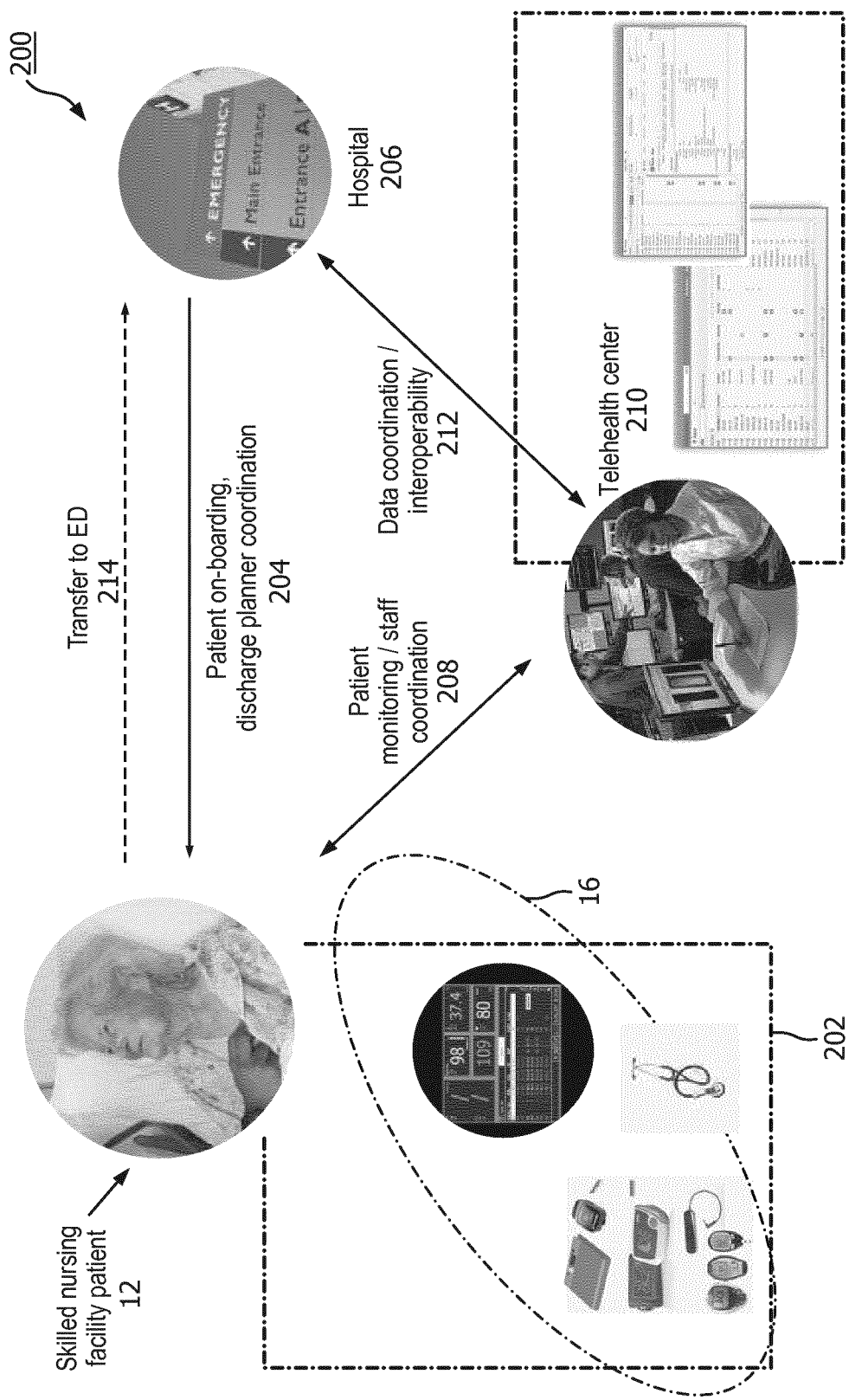
FIG. 2 illustrates an example of a telehealth system.

By way of a non-limiting example, system 10 may be used in a telehealth system similar to and/or the same as telehealth system 200 illustrated in FIG. 2. As shown in FIG. 2, a SNF patient 12 is monitored at a SNF 202 using various sensors 16. SNF patient 12 may be monitored and/or further treated at SNF 202 after being discharged 204 from a hospital 206, for example. Information obtained during monitoring may be communicated 208 to a central telehealth center 210 and/or a central care coordinator 14 where the information may be analyzed (e.g., as described herein). Central telehealth center 210 may, in turn, communicate 208, 212 information back and forth between SNF 202 and hospital 206. SNF patient 12 may be transferred 214 to an emergency department (ED) at hospital 206 if necessary based on the analyzed and/or other information.

Returning to FIG. 1, in some embodiments, system 10 comprises sensors 16, computing devices 18, one or more processors 20, electronic storage 22, external resources 24, and/or other components.

Sensors 16 are configured to generate output signals conveying information related to one or more physiological characteristics of patients 12. The physiological characteristics of patients 12 may be and/or be included in care information, SNF enhancement information, and/or other information collected and/or otherwise obtained by system 10 (e.g., as described below). In some embodiments, sensors 16 include but are not limited to equipment used in hospitals, doctor's offices, and/or other medical facilities, in the homes of patients 12, and/or in other locations to monitor vital signs and/or other physiological information (e.g., pulse rate monitors, blood pressure monitors, blood oxygenation monitors, glucose monitors, weight scales, thermometers, electrocardiogram (EKG) equipment, childbirth labor contraction monitors, etc.), test equipment (e.g., imaging equipment such as an MRI and/or an x-ray machine, an ultrasound, electroencephalogram (EEG) equipment, etc.), equipment for treating patients 12 (e.g., respirators/ventilators, light therapy devices, etc.), and/or other devices. Sensors 16 may comprise one or more sensors that generate such information directly. For example, sensors 16 may include electrodes configured to detect electrical activity in the heart of a patient 12, light based sensors coupled with a finger of a patient 12 configured to detect a pulse rate and/or a blood chemistry (e.g., an oxygen level) of a patient 12, a blood pressure cuff configured to facilitate determination of the blood pressure of a patient 12, a thermometer coupled to a patient 12, and/or other sensors. Sensors 16 may comprise one or more sensors that generate such information indirectly. For example, one or more sensors 16 may include a camera configured to generate an output based on images of patients 12 (e.g., a heart rate of a patient 12, respiration of a patient 12, a temperature of a patient 12, an oxygen saturation level of a patient 12, and/or other characteristics of patients 12). Although sensors 16 are illustrated in FIG. 1 at a single location near patients 12, this is not intended to be limiting. Sensors 16 may include sensors disposed in a plurality of locations, such as for example, coupled (in a removable manner) with clothing of patients 12, worn by patients 12 (e.g., as a headband, wristband, a blood pressure cuff, a finger clip, etc.), positioned to point at patients 12 (e.g., a camera), temporarily held and/or supported by a patient 12 (e.g., a thermometer), and/or in other locations. In some embodiments, information from one or more sensors 16 may be automatically transmitted to one or more computer devices 18, one or more remote servers, or other destinations via one or more networks (e.g., local area networks, wide area networks, the Internet, etc.).

Computing devices 18 are configured to provide an interface between patients 12, caregivers 14, and system 10. In some embodiments, computing devices 18 are associated with individual caregivers 14, a central caregiver coordinator, and/or other users. Computing devices 18 are configured to provide information to and/or receive information from patients 12, caregivers 14, and/or other users. Computing devices 18 include a user interface and/or other components. The user interface may be and/or include a graphical user interface configured to present caregivers 14 with views and/or fields configured to receive entry and/or selection of information related to patients 12 (SNF patients), present scores for the individual patients 12 as a triaged list of individual SNF patients (e.g., as described below), provide instructions to caregivers 14 based on the scores, and/or provide and/or receive other information. In some embodiments, the user interface includes a plurality of separate interfaces associated with a plurality of computing devices 18, processors 20, and/or other components of system 10, for example. In some embodiments, one or more computing devices 18 may comprise one or more sensors 16 (e.g., desktop computers, laptop computers, tablet computers, smartphones, or other computing devices that may comprise such sensors 16).

In some embodiments, computing devices 18 are configured to provide the user interface, processing capabilities, databases, and/or electronic storage to system 10. As such, computing devices 18 may include processors 20, electronic storage 22, external resources 24, sensors 16, and/or other components of system 10. In some embodiments, computing devices 18 are connected to a network (e.g., the internet). In some embodiments, computing devices 18 do not include processor 20, electronic storage 22, external resources 24, sensors 16, and/or other components of system 10, but instead communicate with these components via the network. The connection to the network may be wireless or wired. For example, processor 20 may be located in a remote server and may wirelessly cause display of the triaged list of individual SNF patient scores via the user interface to a caregiver 14 on a computing device 18 associated with that caregiver (e.g., a doctor, a nurse, a central caregiver coordinator, etc.). In some embodiments, computing devices 18 are laptops, desktop computers, smartphones, tablet computers, and/or other computing devices.

Examples of interface devices suitable for inclusion in the user interface include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that computing devices 18 include a removable storage interface. In this example, information may be loaded into computing devices 18 from removable storage (e.g., a smart card, a flash drive, a removable disk) that enables caregivers 14 and/or other users to customize the implementation of computing devices 18. Other exemplary input devices and techniques adapted for use with computing devices 18 and/or the user interface include, but are not limited to, an RS-232 port, RF link, an IR link, a modem (telephone, cable, etc.) and/or other devices.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG.

1 as a single entity, this is for illustrative purposes only. In some embodiments, processor 20 may comprise a plurality of processing units. These processing units may be physically located within the same device (e.g., a server), or processor 20 may represent processing functionality of a plurality of devices operating in coordination (e.g., one or more servers, computing devices 18, sensors 16, devices that are part of external resources 24, electronic storage 22, and/or other devices.)

In some embodiments, processor 20, sensors 16, external resources 24, computing devices 18, electronic storage 22, and/or other components may be operatively linked via one or more electronic communication links. For example, such electronic communication links may be established, at least in part, via a network such as the Internet, and/or other networks. It will be appreciated that this is not intended to be limiting, and that the scope of this disclosure includes embodiments in which these components may be operatively linked via some other communication media. In some embodiments, processor 20 is configured to communicate with sensors 16, external resources 24, computing devices 18, electronic storage 22, and/or other components according to a client/server architecture, a peer-to-peer architecture, and/or other architectures.

As shown in FIG. 1, processor 20 is configured via machine-readable instructions to execute one or more computer program components. The one or more computer program components may comprise one or more of a care information component 30, an SNF enhancement information component 32, a care information score component 34, an SNF enhancement score component 36, a combined score component 38, a risk/intervention component 40, and/or other components. Processor 20 may be configured to execute components 30, 32, 34, 36, 38, and/or 40 by software; hardware; firmware; some combination of software, hardware, and/or firmware; and/or other mechanisms for configuring processing capabilities on processor 20.

It should be appreciated that although components 30, 32, 34, 36, 38, and 40 are illustrated in FIG. 1 as being co-located within a single processing unit, in embodiments in which processor 20 comprises multiple processing units, one or more of components 30, 32, 34, 36, 38, and/or 40 may be located remotely from the other components. The description of the functionality provided by the different components 30, 32, 34, 36, 38, and/or 40 described below is for illustrative purposes, and is not intended to be limiting, as any of components 30 32, 34, 36, 38, and/or 40 may provide more or less functionality than is described. For example, one or more of components 30, 32, 34, 36, 38, and/or 40 may be eliminated, and some or all of its functionality may be provided by other components 30, 32, 34, 36, 38, and/or 40. As another example, processor 20 may be configured to execute one or more additional components that may perform some or all of the functionality attributed below to one of components 30, 32, 34, 36, 38, and/or 40.

Care information component 30 is configured to obtain care information for the larger population of SNF patients. The care information comprises physiological information collected by caregivers 14 during care for the larger population of SNF patients. In some embodiments, the care information includes information conveyed by answers to survey questions, manually recorded information, test results, output from sensors 16 and/or other medical devices, information in medical care provider databases (e.g., Medicare databases) and/or other care information. In some embodiments, the care information includes, for example, lab values, blood pressure, pulse rate, respiratory rate, temperature, $O_2$ saturation levels, weight, information conveyed by answers to disease-specific surveys, prescribed medications, dietary information, intake and/or output dates, and/or other information. In some embodiments, care information component 30 is configured to facilitate direct entry and/or selection of care information via computing devices 18. In some embodiments, care information component 30 obtains care information stored in electronic storage 22, information stored in electronic medical record systems and/or other medical information systems of care providers associated with system 10 (e.g., servers and/or other databases that are part of external resources 24 such as Medicare databases, etc.), and/or information from other sources. In some embodiments, care information component 30 obtains care information included in the output signals from sensors 16.

SNF enhancement information component 32 is configured to facilitate collection of SNF enhancement information for the larger population of SNF patients. The SNF enhancement information comprises information related to SNF specific care provided to the larger population of SNF patients. In some embodiments, the SNF enhancement information comprises information related to one or more of fluid intake and/or output from, bowel movements of, oral food intake of, behavior of, wound assessment and/or treatment of, blood glucose of, therapy received by, a level of physical assistance received by, individual SNF patients, and/or other information. For example, such information may include fluid intake/output amounts; whether and/or what types of drains and/or other devices are used; color of fluid output; an amount, timing, frequency, and/or consistency of bowel movements; a quantity of food eaten; a percentage of meals consumed; behavioral notes; a record of wound types (e.g., pressure, surgical, traumatic, etc.), wound size (e.g., length, width, depth), a type of exudate, a wound odor, and/or names and/or types of support surfaces and/or other pressure reducing devices used for wound treatment; information related to blood glucose and/or point of care (POC) finger sticks; minutes spent in therapy per type per day (e.g., obtained from physical therapy (PT)/occupational therapy (OT)/speech language pathology (SLP) flow sheets); information related to activities of daily living (ADL) support/assistance by shift (e.g., using standard minimum data set (MDS) legend/codes); an observed activity level and/or amount of activity; pain scores and/or other rankings; and/or other information.

In some embodiments, the SNF enhancement information comprises information recorded in one or more flow sheets associated with an SNF. In some embodiments, facilitating the collection of the SNF enhancement information comprises causing display of one or more fields in a view of a graphical user interface configured to receive entry and/or selection of the SNF enhancement information. In some embodiments, SNF enhancement information component 32 obtains SNF enhancement information stored in electronic storage 22, SNF enhancement information stored in electronic medical record systems and/or other medical information systems of care providers associated with system 10 (e.g., servers and/or other databases that are part of external resources 24 such as Medicare databases, etc.), and/or SNF enhancement information from other sources. In some embodiments, SNF enhancement information component 32 obtains SNF enhancement information included in the output signals from sensors 16.

Figure 3:
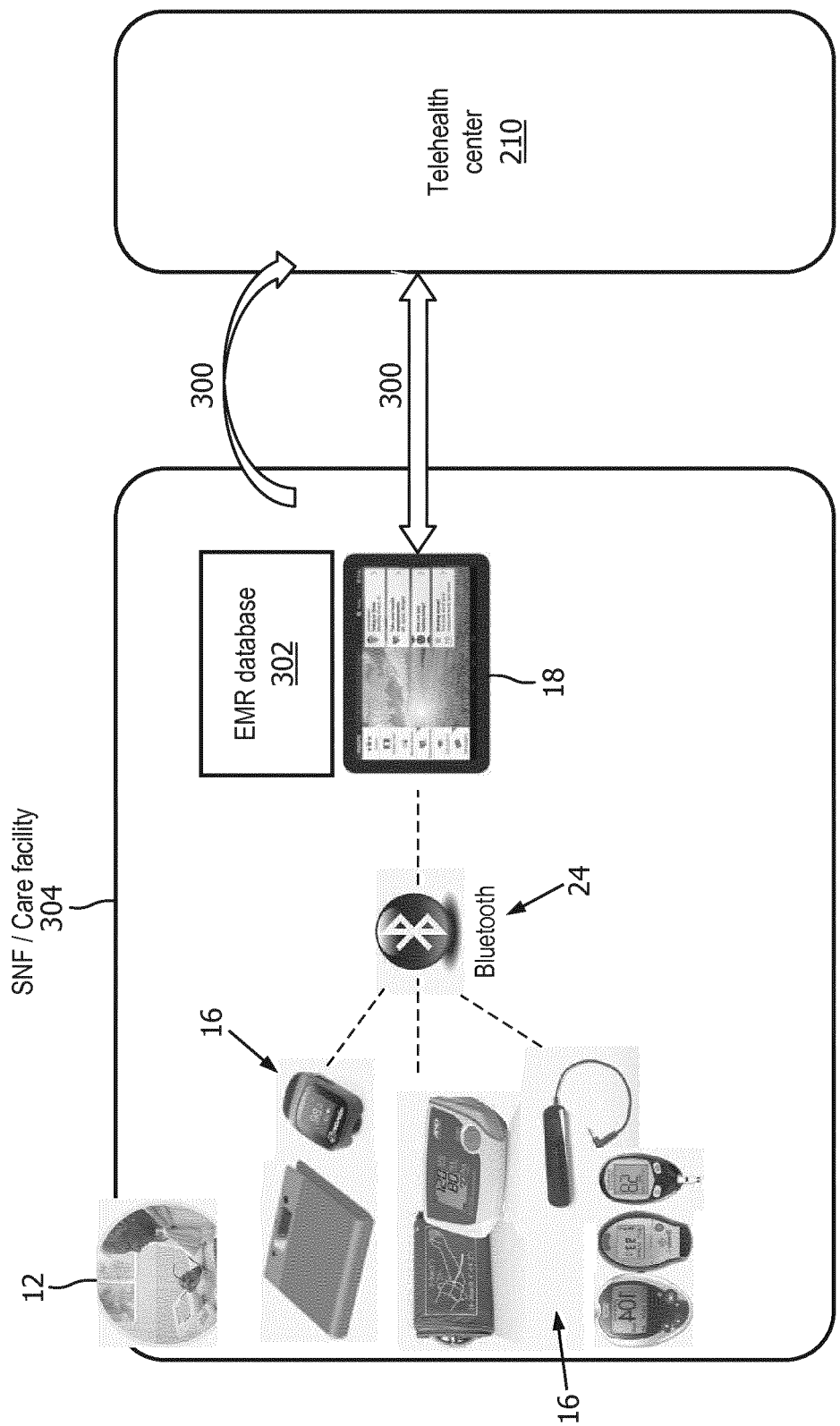
FIG. 3 illustrates an example of obtaining care information and/or SNF enhancement information.

By way of a non-limiting example, FIG. 3 illustrates obtaining care information and/or SNF enhancement information 300. As described above, care information and SNF enhancement information are separate types of information, but the ways in which they are obtained may be similar and/or the same. In the example shown in FIG. 3, information 300 is obtained from both an electronic medical records database 302 associated with a SNF and/or other care facility 304, and from a computing device 18 associated with facility 304. In this example, information 300 provided by computing device 18 was collected via one or more sensors 16 configured to wirelessly (e.g., via Bluetooth components included in external resources 24) communicate with computing device 18.

Figure 4:
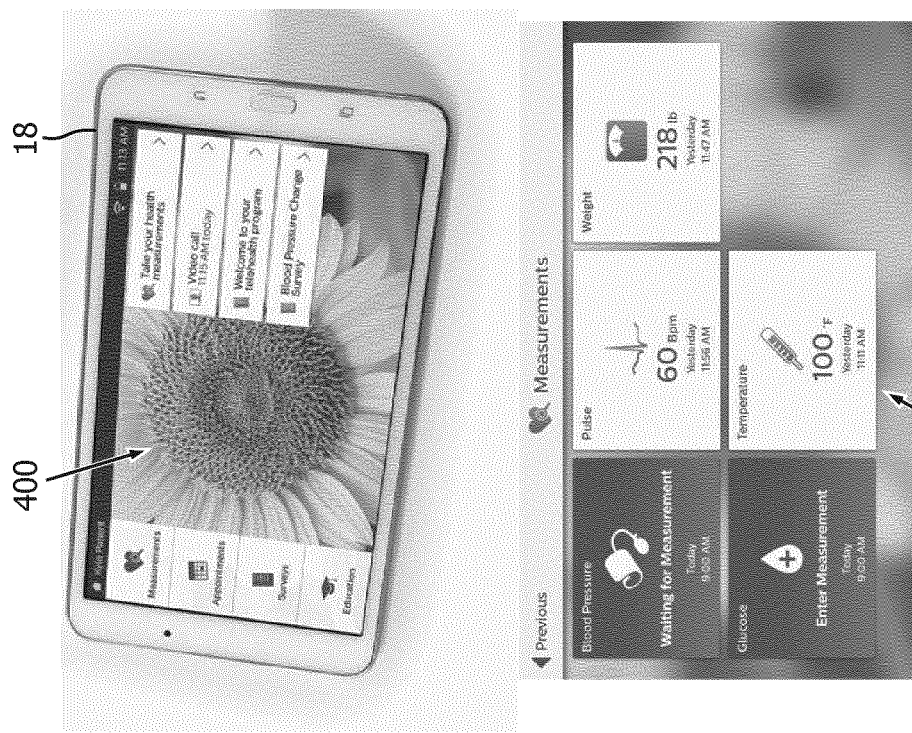
FIG. 4 illustrates facilitating collection of care information and/or SNF enhancement information via views of a graphical user interface presented via a computing device.
Figure 4:
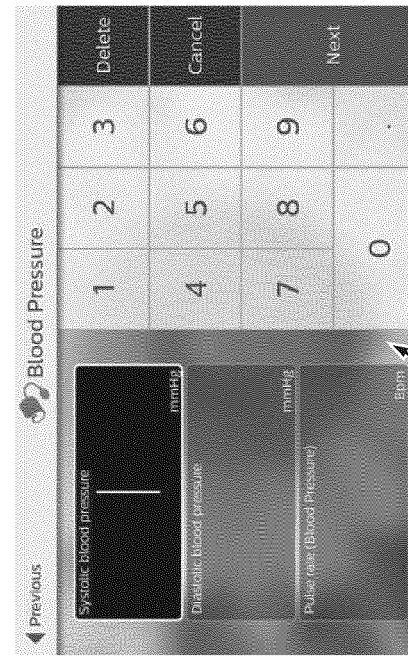

FIG. 4 illustrates facilitating collection of care information and/or SNF enhancement information via views 400, 402, 406 of a graphical user interface presented via a computing device 18. In the example shown in FIG. 4, entry and/or selection of blood pressure information is facilitated. View 400 presents selectable fields that specify different care activities related to a patient that may be performed for the patient. View 402 illustrates that a measurements field was selected in view 400 and presents various selectable field options for entering different types of physiological information for the patient. View 406 indicates that the blood pressure field was selected from view 402 and presents a caregiver with fields for entering and/or selecting blood pressure information. FIG. 4 is not intended to be limiting. For example, instead of manual entry of blood pressure information, the blood pressure information may be automatically communicated from a blood pressure sensor 16 (FIG. 1). Or, instead of facilitating the entry of blood pressure information, views 400, 402, and 406 may facilitate the entry and/or selection of information from a SNF flow sheet.

Returning to FIG. 1, care information score component 34 is configured to determine care information scores for individual SNF patients (patients 12). The care information scores are determined based on the obtained care information. The care information scores are determined using a first set of severity weights associated with individual components of the care information. In some embodiments, the weighted individual components of the care information comprise care measurements, observed care issues, care surveys, discharge information, readmission information, unexpected measurement information, and/or other components. In some embodiments, the weighted individual components of the SNF enhancement information are weighted as shown in Table II (though this is not intended to be limiting).

TABLE I

|  | Low | Medium | High | None/Other |
|---|---|---|---|---|
| Measurement | 5 | 10 | 15 | 0 |
| Issue | 0 | 0 | 3 | 0 |
| Survey | 0 | 1 | 4 | 0 |
| Discharge Score | N/A | N/A | N/A | 1 |
| Unexpected measurement | N/A | N/A | N/A | 6 |
| Readmission Score | N/A | N/A | N/A | 1 |

SNF enhancement score component 36 is configured to determine SNF enhancement scores for the individual SNF patients (patients 12) based on the SNF enhancement information. The SNF enhancement scores are determined using a second set of severity weights associated with individual components of the SNF enhancement information. The second set of severity weights are heavier than the first set of severity weights such that the SNF enhancement scores are weighted more heavily than the care information scores for the individual SNF patients (e.g., the numbers in Table II below are larger than the numbers in Table I). In some embodiments, the weighted individual components of the SNF enhancement information comprise SNF surveys, SNF measurements, SNF issues, SNF lab results, and/or other components. In some embodiments, the weighted individual components of the SNF enhancement information are weighted as shown in Table II (though this is not intended to be limiting).

TABLE II

|  | Low | Medium | High | None |
|---|---|---|---|---|
| Surveys | 10 | 15 | 20 | 0 |
| Measurements | 10 | 15 | 20 | 0 |
| Issues | 15 | 25 | 30 | 0 |
| Laboratory Results | 5 | 10 | 15 | 0 |

In some embodiments, determining care information scores and/or SNF enhancement scores includes determining individual factors of the weighted individual components. The weighted individual components of the care information and/or the SNF enhancement information comprise multiple individual factors that correspond to the obtained care and/or SNF enhancement information. The factors are weighted according to Tables I (e.g., for factors of the weighted individual components of the care information) and II (e.g., for factors of the weighted individual components of the SNF enhancement information) to determine the contribution of a particular factor to the care information scores and/or the SNF enhancement scores respectively.

Examples of these factors for the weighted individual components of the SNF enhancement information are listed in Examples 1-4 below. SNF enhancement score component 36 (and similarly care information score component 34) is configured to categorize the individual factors by different assessment levels for an individual factor based on the SNF enhancement information (and similarly the care information for care information score component 34). The different assessment levels correspond to different (e.g., none, low, medium, high) severity ratings for that factor. The different assessment levels and/or severity ratings may be determined at manufacture of system 10, determined and/or adjusted via a computing device 18 (e.g., customized by and/or for a specific SNF), and/or determined by other methods. As an example, behavioral observations are a factor in the SNF issues component (see Example 3 below). Assessed hallucinations and/or delusions are rated as a high severity. As such, any hallucinations and/or delusions by a patient 14 would therefore contribute a value of 30 to the SNF enhancement score because hallucinations and/or delusions are flagged as high severity, and high severity issues contribute a value of 30 to the SNF enhancement score according to Table II.

This process may be repeated for other factors related to the same and/or other weighted individual components of the SNF enhancement information (and similarly for factors related to the weighted individual components of the care information) to determine the SNF enhancement scores for patients 12. For example, this process may be repeated for SNF enhancement factors listed in Examples 1-4 below such as fluid intake/output amounts; whether and/or what types of drains and/or other devices are used; color of fluid output; an amount, timing, frequency, and/or consistency of bowel movements; a quantity of food eaten; a percentage of meals consumed; behavioral notes; a record of wound types (e.g., pressure, surgical, traumatic, etc.), wound size (e.g., length, width, depth), a type of exudate, a wound odor, and/or names and/or types of support surfaces and/or other pressure reducing devices used for wound treatment; information related to blood glucose and/or (POC) finger sticks; minutes spent in therapy per type per day (e.g., obtained from PT/OT/SLP flow sheets); information related to ADL support/assistance by shift (e.g., using standard MDS legend/codes); an observed activity level and/or amount of activity; pain scores and/or other rankings; and/or other factors.

Combined score component 38 is configured to combine the care information scores with the SNF enhancement scores for the individual SNF patients to determine a combined score that indicates risk of clinical deterioration and/or a need for medical intervention for the individual SNF patients. In some embodiments, this combination may comprise adding the care information score to the SNF enhancement score for an individual patient 12. In some embodiments, combining may comprise performing multiple mathematical operations with the care information score and the SNF enhancement score for patient 12.

In some embodiments, combined score component 38 may be configured to assign weights to the care information scores compared to the SNF enhancement scores according to the number of days an SNF patient receives care in the SNF. Combined score component 38 may be configured to assign different weights week by week to reflect patients recovering from being acutely ill, then sub-acutely ill, then in a recovered state upon discharge. Some protocols and/or monitoring may occur for 90 days or more (e.g., more than four weeks as in the examples below), but there are many possible examples of many possible combinations for four weeks of monitoring/weighted scoring. A first possible example includes: (a) Week 1: eCC (care information) score 1x, score for ePAC-SNF (SNF enhancement score)1x; (b) Week 2: eCC score 1x, score for ePAC-SNF 2x; (c) Week 3: eCC score 1x, Score for ePAC-SNF 3x; (d) Week 4: eCC score 1x, score for ePAC-SNF 4x. A second possible example includes: (a) Week 1: eCC score 1x, score for ePAC-SNF 4x; (b) Week 2: eCC score 1x, score for ePAC-SNF 3x; (c) Week 3: eCC score 1x, score for ePAC-SNF 2x; (d) Week 4: eCC score 1x, score for ePAC-SNF 1x. A third possible example includes (in this example of weighting, the increased weight for week 1 reflects the acuity of the patient upon hospital discharge whereas week 3 reflects the increased risk due to exacerbations of the patient's underlying illnesses): (a) Week 1: eCC score 1x, score for ePAC-SNF 2x; (b) Week 2: eCC score 1x, score for ePAC-SNF 1x; (c) Week 3: eCC score 1x, score for ePAC-SNF 2x; (d) Week 4: eCC score 1x, score for ePAC-SNF 1x.

In some embodiments, combined score component 38 may be configured to assign weights to the care information scores compared to the SNF enhancement scores based on the season of the year and/or other factors that affect seasonal variations and/or other variations in illness. For example, November-January may weighted as a higher risk such that for February-October, the eCC scores are weighted 1x and the scores for ePAC-SNF are weighted 1x, while in November-January the eCC scores are weighted 2x and the scores for ePAC-SNF are weighted 1x. In some embodiments, weights may be applied based on demographic information. For example, for patients on Medicare without Medicaid insurance, combined score component 38 may weigh the eCC score 1x and the score for ePAC-SNF 1x. For patients with both Medicare and Medicaid insurance the eCC score may be weighted 2x and the ePAC-SNF score may be weighted 1x. In some embodiments, combined score component 38 may be configured to weight eCC scores versus scores for ePAC-SNF based on other factors such as a number of conditions (e.g., for <5 diseases weight the eCC score 1x and the score for ePAC-SNF 1x; for >6 diseases weight the eCC score 1x and the score for ePAC-SNF 2x), a number of medications (e.g., for <19 medications weight the eCC score 1x and the score for ePAC-SNF 1x; for >20 meds weight the eCC score 1x and the score for ePAC-SNF 2x), PHQ-9 results, BIMS results, Morisky results, and/or other factors.

In some embodiments, combined score component 38 may be configured to weight scoring for eCC (the care information score) based on the number of measurements required in a protocol and weight those per flag (e.g., as described herein). For example, two red flags out of two measurements would receive a higher weight than two red flags out of four measurements.

Figure 5:
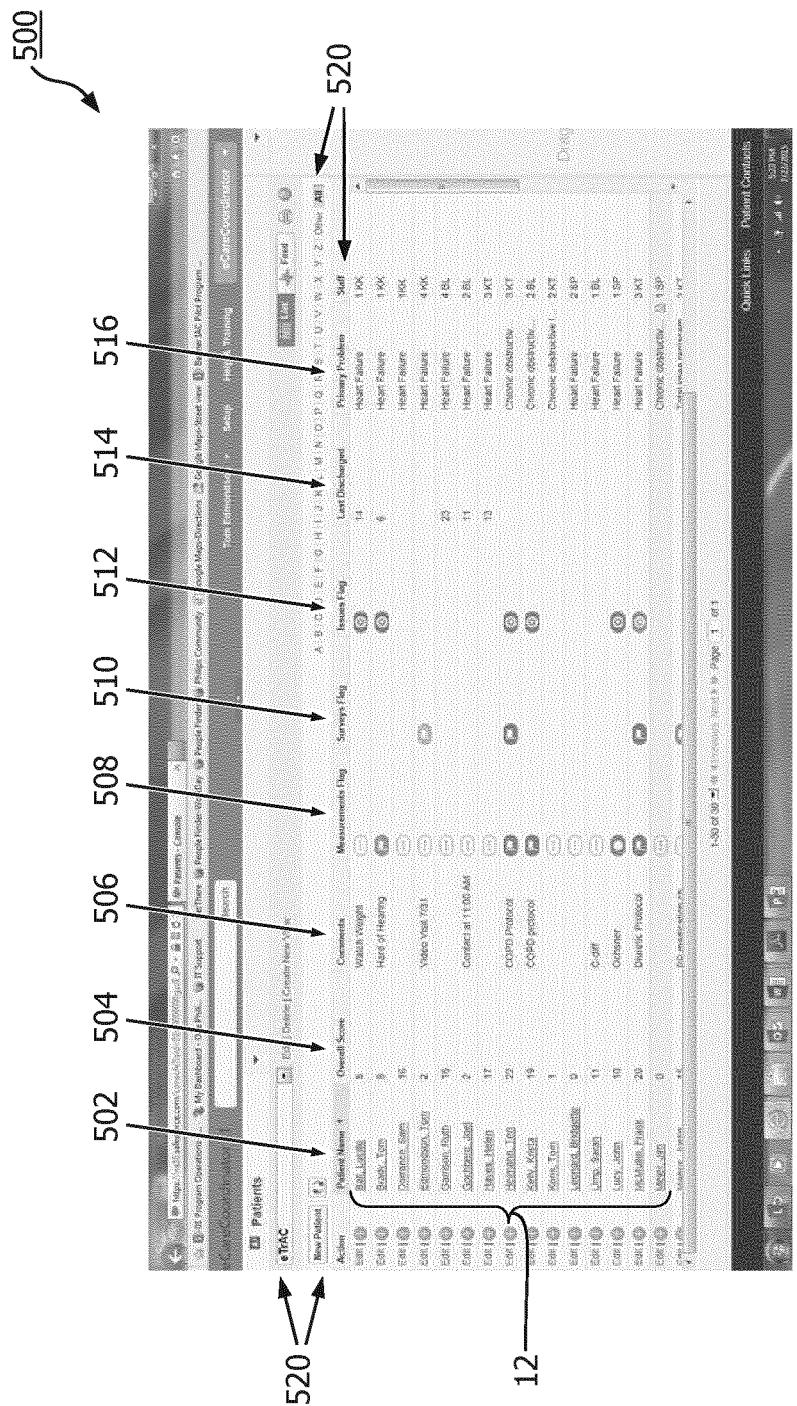
FIG. 5 illustrates a view of a user interface that displays combined scores for patients.

Risk/intervention component 40 is configured to cause display of the combined scores for the individual SNF patients (patients 12) as a triaged list of individual SNF patients in a view of a graphical user interface displayed on one or more computing devices 18. In some embodiments, the triaged list may be and/or include a listing of patients 12 ranked by their corresponding overall scores (e.g., highest overall score to lowest overall score). In some embodiments, risk/intervention component 40 is configured to display the combined scores for the individual SNF patients without generating a triaged list. For example, FIG. 5 illustrates a view 500 of a user interface (e.g., displayed on computing devices 18). View 500 includes patient name field 502, overall score field 504, a comments field 506, a measurements flag field 508, a surveys flag field 510, an issues flag field 512, a last discharged field 514, a primary problem field 516, and various fields 520 that facilitate care for and/or tracking of patients 12. Patient name field 502 lists the names of patients 12. Overall score field 504 lists overall scores (e.g., determined as described above) for the individual patients 12. In FIG. 5, patients 12 are not ordered by their overall scores. Comments field 506 lists general comments related to health issues experienced by patients 12. Flag fields 508-512 display color coded flags (further described below) that indicate whether a patient 12 has items (e.g., measurements, surveys, issues) that a caregiver 14 (FIG. 1) may wish to review. Field 514 lists the number of days since a patient was last discharged from a hospital. In the example shown in FIG. 5, field 514 is left blank if that number is more than 30 days (this number of days is not intended to be limiting and may be any number that allows system 10 to operate as described herein).

Figure 6:
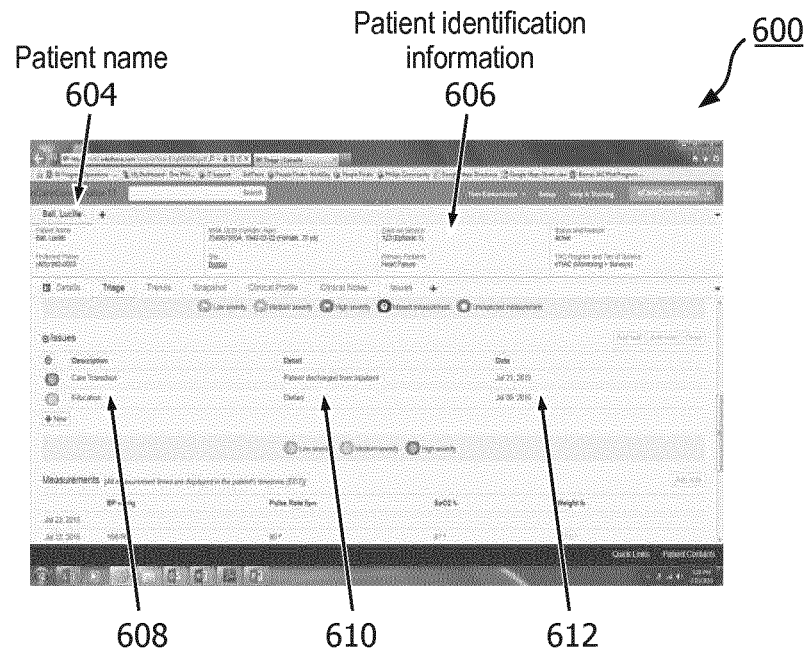
FIG. 6 illustrates two additional example views of the user interface for a particular example patient.
Figure 6:
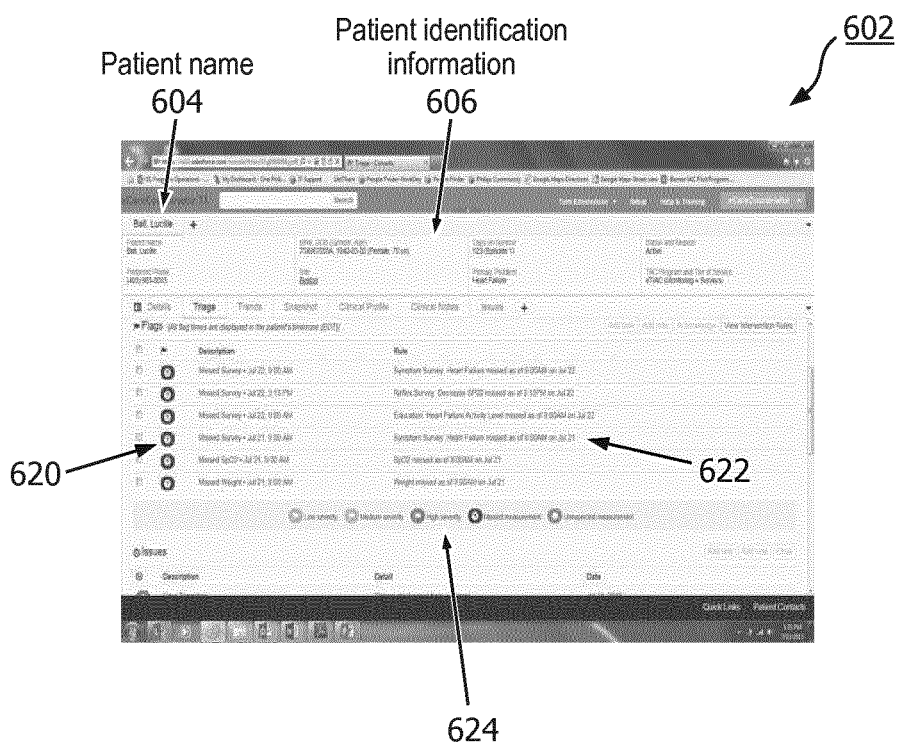

In some embodiments, risk/intervention component 40 is configured to cause display of views of the user interface in addition to and/or instead of views that include the combined scores for the individual SNF patients (patients 12). For example, FIG. 6 illustrates two additional example views 600, 602 of the user interface for a particular example patient 12. Views 600 and/or 602 may be presented to a caregiver 14 responsive to the caregiver selecting the patient's name in field 502 of view 500, for example. Views 600 and 602 both include a patient name field 604 and patient identification information fields 606. View 600 summarizes recent issues for the patient in an issues list field 608. Details list field 610 provides details about the individual issues listed in field 608. Date field 612 lists a date that corresponds to the issues in field 608. View 602 includes a flag summary list field 620 that lists flagged events for the patient (e.g., a missed survey, a missed SpO$_2$ measurement, a missed weight measurement, etc.). View 602 also includes an information list field 622 that provides additional information about the flagged events, and a flag color code key field 624 that displays flag colors and corresponding event severities.

It should be noted that FIG. 5 and FIG. 6 are not intended to be limiting. Risk/intervention component 40 may be configured to cause display of any number of views and/or fields of the user interface that allow system 10 to function as described herein. For example, view 600 may have just as easily been shown presenting information related to measurements, surveys, and so on, and/or any other information that may be useful to a caregiver 14 using system 10.

As described above, in some embodiments, risk/intervention component 40 (FIG. 1) is configured to cause display of color coded flags (e.g., red corresponding to severe, orange corresponding to less sever, yellow corresponding to even less severe, and so on) that correspond to assessment and/or severity levels of the weighted individual components of the SNF enhancement information and/or the factors included in the weighted individual components. For example, for an individual patient 12 (FIG. 1), risk/intervention component 40 may display color coded flags for SNF surveys, SNF measurements, SNF issues, SNF lab results (e.g., as illustrated in FIGS. 5 and 6), and/or other components.

By way of a non-limiting example, a high/red flag may be associated with a specific symptom, measurement, issue, and/or lab data point that warrants an in-depth assessment and/or examination by a monitoring clinician. This flag usually predicts clinical deterioration in real-time and/or in the near future. For example, a missed survey, a missed measurement, and/or a particular survey result may trigger a red flag. An appetite much worse than usual may trigger a high/red flag. PT/OT/SLP that is less than 30 minutes may trigger a high/red flag. A medium/yellow flag may be associated with a symptom, measurement, issue, and/or lab data point that may be assigned following an analysis of a pattern and/or trend in data points, and/or an individual data point that is concerning to the monitoring clinician and may warrant in-depth assessment. A low flag may facilitate awareness by the monitoring clinician but may not require a change in assessment and/or a treatment plan.

Risk/intervention component 40 may display color coded flags for individual factors based on their associated assessment levels such as those listed in Examples 1-4 below (e.g., fluid intake/output amounts; whether and/or what types of drains and/or other devices are used; color of fluid output; an amount, timing, frequency, and/or consistency of bowel movements; a quantity of food eaten; a percentage of meals consumed; behavioral notes; a record of wound types (e.g., pressure, surgical, traumatic, etc.), wound size (e.g., length, width, depth), a type of exudate, a wound odor, and/or names and/or types of support surfaces and/or other pressure reducing devices used for wound treatment; information related to blood glucose and/or (POC) finger sticks; minutes spent in therapy per type per day (e.g., obtained from PT/OT/SLP flow sheets); information related to ADL support/assistance by shift (e.g., using standard MDS legend/codes); an observed activity level and/or amount of activity; pain scores and/or other rankings; and/or other factors).

Returning to FIG. 1, in some embodiments, risk/intervention component 40 is configured to control a medical device associated with an individual SNF patient (patient 12) to treat the individual SNF patient based on a combined score for the individual patient. For example, based on a combined score for a patient 12 that breaches a threshold value and indicates risk of clinical deterioration and/or a need for medical intervention in a diabetic patient 12, risk/intervention component 40 may cause an insulin pump (e.g., included in external resources 24) to pump insulin into patient 12. In one use case, responsive to the combined score breaching a first threshold value indicative of a need for a first amount of insulin, risk/intervention component 40 may automatically cause the insulin pump to pump the first amount of insulin into patient 12. Responsive to the combined score breaching a second threshold value (different from the first threshold value) indicative of a need for a second amount of insulin (different from the first amount of insulin), risk/intervention component 40 may automatically cause the insulin pump to pump the second amount of insulin into patient 12. In another use case, the insulin pump may be locked (e.g., software-based lock) to prevent patient 12 or other user from excess pumping of insulin into patient 12 (e.g., to protect older, frail, disabled, and/or medically ill patients who may be more sensitive to excess insulin). Responsive to the combined score breach a threshold value (e.g., the first, second, or other threshold value), risk/intervention component 40 may automatically enable the insulin pump to pump an amount of insulin into the patient (e.g., by unlocking a software-based lock that prevents the insulin pump from releasing insulin to enable the respective first, second, or other amount of insulin to be pumped into patient 12). Risk/intervention component 40 may alternatively or additionally cause an alert to notify one or more users of the need for insulin. Such examples are not intended to be limiting. Such criteria and/or threshold values for the combined scores, factor severity levels, and/or the individual patients themselves (e.g., criteria/thresholds programmed for a diabetic patient may be different that criteria/thresholds programmed for a patient who suffers from dementia) may be determined at manufacture of system 10, determined and/or adjusted via computing devices 18, and/or determined by other methods.

Other examples (these are not intended to be limiting) of risk/intervention component 40 controlling a medical device associated with an individual SNF patient (patient 12) to treat the individual SNF patient based on a combined score for the individual patient include controlling CPAP/Bi-PAP devices to change pressure levels, controlling ventilators to adjust an O$_2$ supply, controlling IV pumps with inotropes to adjust doses; controlling SMART inhalers (e.g., for SNF patients with asthma and/or COPD) to send alerts when it is time to take a preventive dose of medication, and/or other examples.

In some embodiments, risk/intervention component 40 is configured to direct treatment of an individual SNF patient (patient 12) based on a combined score for the individual patient by providing instructions to a caregiver 14 via a view of the graphical user interface displayed on a computing device 18. For example, risk/intervention component 40 may cause the graphical user interface to display a recommendation that wound dressings of a patient 12 be changed, recommended dietary changes, recommended increases and/or decreases in an amount of physical therapy, a recommendation that a patient 12 be admitted to the hospital, and/or other recommendations. In some embodiments, risk/intervention component 40 is configured to direct treatment of an individual SNF patient (patient 12) based on the severity flags associated with factors of, and/or the weighted individual components themselves, of the SNF enhancement information. Risk/intervention component 40 may, for example, provide instructions to a caregiver 14 via a view of the graphical user interface displayed on a computing device 18 based on a trend in severity flags over time for a particular component and/or factors that indicate abnormal and/or otherwise worrisome results, behaviors, and/or other characteristics of a patient 12.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may be (in whole or in part) a separate component within system 10, or electronic storage 22 may be provided (in whole or in part) integrally with one or more other components of system 10 (e.g., a computing device 18, processor 20, etc.). In some embodiments, electronic storage 22 may be located in a server together with processor 20, in a server that is part of external resources 24, in computing devices 18 associated with caregivers 14, and/or in other locations. Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via computing devices 18 and/or other external computing systems, information received from external resources 24, information received from sensors 16, and/or other information that enables system 10 to function as described herein. By way of a non-limiting example, electronic storage 22 may store the combined scores for the individual SNF patients (patients 12) determined by combined score component 38 of processor 20.

External resources 24 include sources of information (e.g., databases, websites, etc.), external entities participating with system 10 (e.g., a medical records system of a health care provider that stores care information and/or SNF enhancement information for patients 12), external home monitoring systems, one or more servers outside of system 10, a network (e.g., the internet), electronic storage, equipment related to Wi-Fi technology, equipment related to Bluetooth® technology, data entry devices, sensors, scanners, and/or other resources. In some implementations, some or all of the functionality attributed herein to external resources 24 may be provided by resources included in system 10. External resources 24 may be configured to communicate with processor 20, computing devices 18, sensors 16, electronic storage 22, and/or other components of system 10 via wired and/or wireless connections, via a network (e.g., a local area network and/or the internet), via cellular technology, via Wi-Fi technology, and/or via other resources.

Figure 7:
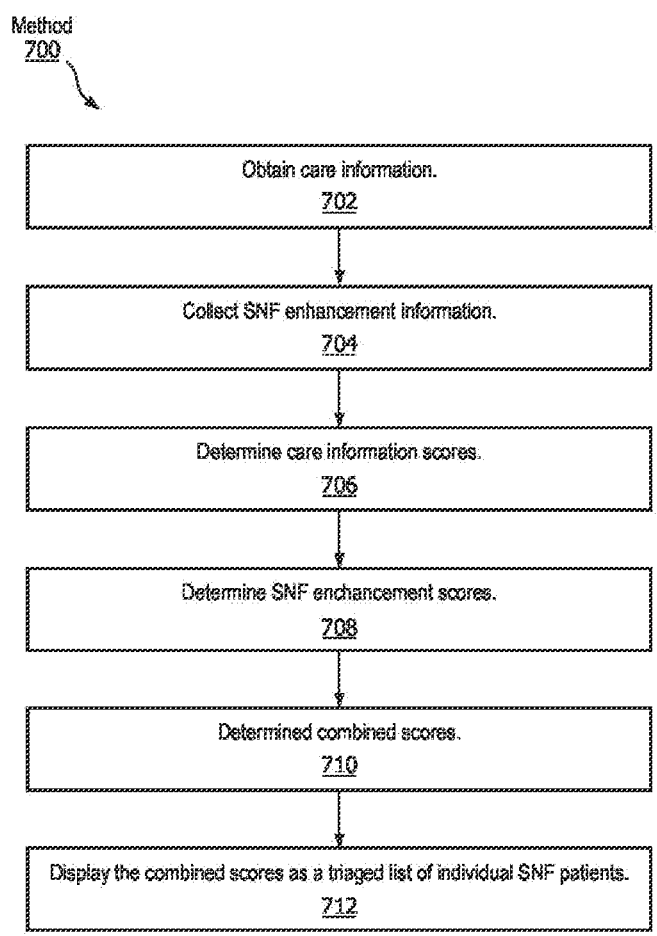
FIG. 7 illustrates a method for facilitating computer-assisted care for SNF patients at risk of clinical deterioration and/or in need of medical intervention relative to a larger population of SNF patients.

FIG. 7 illustrates a method 700 for facilitating computer-assisted care for SNF patients at risk of clinical deterioration and/or in need of medical intervention relative to a larger population of SNF patients. Method 700 may be performed with a display system. The system comprises a computing device including a user interface, one or more hardware processors, and/or other components. The one or more hardware processors are configured by machine readable instructions to execute computer program components. The computer program components include a care information component, an SNF enhancement information component, a care information score component, an SNF enhancement score component, a combined score component, a display component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, care information for the larger population of SNF patients is obtained. The care information comprises physiological information collected by caregivers (e.g., including manually recorded information, test results, output from medical devices, etc.) during care for the larger population of SNF patients. In some embodiments, operation 702 is performed by a processor component the same as or similar to care information component 30 (shown in FIG. 1 and described herein).

At an operation 704, collection of SNF enhancement information for the larger population of SNF patients is facilitated. The SNF enhancement information comprises information related to SNF specific care provided to the larger population of SNF patients. In some embodiments, the SNF enhancement information comprises information related to one or more of fluid intake and/or output from, bowel movements of, oral food intake of, behavior of, wound assessment and/or treatment of, blood glucose of, therapy received by, a level of physical assistance received by, individual SNF patients, and/or other information. In some embodiments, the SNF enhancement information comprises information recorded in one or more flow sheets associated with a SNF. In some embodiments, facilitating the collection of the SNF enhancement information comprises causing display of one or more fields in a view of a graphical user interface configured to receive entry and/or selection of the SNF enhancement information. In some embodiments, the system further comprises one or more sensors configured to generate output signals conveying information included in the care information (e.g., as described above relative to operation 702) and/or the SNF enhancement information. In some embodiments, operation 704 is performed by a processor component the same as or similar to SNF enhancement information component 32 (shown in FIG. 1 and described herein).

At an operation 706, care information scores are determined for individual SNF patients. The care information scores are determined based on the obtained care information. The care information scores are determined using a first set of severity weights associated with individual components of the care information. In some embodiments, the weighted individual components of the care information comprise care measurements, observed care issues, care surveys, discharge information, readmission information, and/or other components. In some embodiments, operation 706 is performed by a processor component the same as or similar to care information score component 34 (shown in FIG. 1 and described herein).

At an operation 708, SNF enhancement scores are determined for the individual SNF patients based on the SNF enhancement information. The SNF enhancement scores are determined using a second set of severity weights associated with individual components of the SNF enhancement information. The second set of severity weights are heavier than the first set of severity weights such that the SNF enhancement scores are weighted more heavily than the care information scores for the individual SNF patients. In some embodiments, the weighted individual components of the SNF enhancement information comprise SNF surveys, SNF measurements, SNF issues, and SNF lab results. In some embodiments, operation 708 is performed by a processor component the same as or similar to SNF enhancement score component 36 (shown in FIG. 1 and described herein).

At an operation 710, the care information scores are combined with the SNF enhancement scores for the individual SNF patients to determine a combined score that indicates risk of clinical deterioration and/or a need for medical intervention for the individual SNF patients. In some embodiments, operation 710 is performed by a processor component the same as or similar to combined score component 38 (shown in FIG. 1 and described herein).

At an operation 712, the combined scores for the individual SNF patients are displayed as a triaged list of individual SNF patients in a view of a graphical user interface displayed on the one or more computing devices. In some embodiments, operation 712 further comprises controlling a medical device associated with an individual SNF patient to treat the individual SNF patient based on a combined score for the individual patient. In some embodiments, operation 712 further comprises directing treatment of an individual SNF patient based on a combined score for the individual patient by providing instructions to a caregiver via a view of the graphical user interface. In some embodiments, operation 712 is performed by a processor component the same as or similar to risk/intervention component 40 (shown in FIG. 1 and described herein).

EXAMPLES

1. SNF Surveys

| | | | Response Choices | Assessment Level/Severity/Flag |
|---|---|---|---|---|
| Q1 | How are you feeling today? | | | |
| | | A | Better than usual for me | None |
| | | B | Normal or usual for me | None |
| | | C | Worse than usual | Medium |
| | | D | Much worse than usual | High |
| Q2 | How are you sleeping? | | | |
| | | A | Better than usual for me | None |
| | | B | Normal or usual for me | None |
| | | C | Worse than usual | Medium |
| | | D | Much worse than usual | High |
| Q3 | How is your appetite? | | | |
| | | A | Better than usual for me | None |
| | | B | Normal or usual for me | None |
| | | C | Worse than usual | Medium |
| | | D | Much worse than usual | High |
| Q4 | How are your bowel movements? | | | |
| | | A | Better than usual for me | None |
| | | B | Normal or usual for me | None |
| | | C | Worse than usual | Medium |
| | | D | Much worse than usual | High |

2. SNF Measurements

| Source | Name | Description | Assessment | Severity/Flag |
|---|---|---|---|---|
| MDS O0400 | PT/OT/SLP Individual Minutes | | Minutes | |
| | | | 0-30 | High |
| | | | 31-45 | Medium |
| | | | 46-60 | Low |
| | | | 61-90 | None |
| | | | ≥91 | |
| | | PT (if prescribed) | Minutes | |
| | | | 0-30 | High |
| | | | 31-45 | Medium |
| | | | 46-60 | Low |
| | | | 61-90 | None |
| | | | ≥91 | |
| | | OT (if prescribed) | Minutes | |
| | | | 0-30 | High |
| | | | 31-45 | Medium |
| | | | 46-60 | Low |
| | | | 61-90 | None |
| | | | ≥91 | |

-continued

| Source | Name | Description | Assessment | Severity/Flag |
|---|---|---|---|---|
| | | SLP (if prescribed) | Minutes | |
| | | | 0-30 | High |
| | | | 31-45 | Medium |
| | | | 46-60 | Low |
| | | | 61-90 | None |
| | | | ≥91 | |
| MDS G0110 | Functional Status | | ADL | |
| | | | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | A. Bed mobility | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | B. Transfer | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | C. Walk in room | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | D. Walk in corridor | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | D. Walk in corridor | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | E. Locomotion on unit | Self-performance: | |
| | | | 0. Independent | None |
| | | | 1. Supervision | None |
| | | | 2. Limited assistance | Low |

-continued

| Source | Name | Description | Assessment | Severity/Flag |
|---|---|---|---|---|
| | | | 3. Extensive assistance | Medium |
| | | | 4. Total dependence | High |
| | | F. Locomotion off unit | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | G. Dressing | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | H. Eating | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | I. Toilet use | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| | | J. Personal hygiene | Self-performance: | |
| | | | 0. Independent | None |
| | | | 1. Supervision | None |
| | | | 2. Limited assistance | Low |
| | | | 3. Extensive assistance | Medium |
| | | | 4. Total dependence | High |
| Electronic Flow Sheet (such as Care Tracker) | Bowel movement record | | | |
| | | Timing per day | | |
| | | | None for 1 day | None |
| | | | None for 2 days | Low |
| | | | None for 3 days | Medium |
| | | | None for ≥4 days | High |
| | | | 1 | None |
| | | | 2 | Low |
| | | | 3 | Medium |
| | | | ≥4 | High |
| | | Amount | | |
| | | | A smear | Medium |
| | | | Small | Low |
| | | | Medium | None |

-continued

| Source | Name | Description | Assessment | | Severity/Flag |
|---|---|---|---|---|---|
| | | Consistency | Large | | None |
| | | | Extra large | | Low |
| | | | Loose | | Medium |
| | | | Watery | | High |
| | | | Semi-solid | | Low |
| | | | Solid | | None |
| Electronic Flow Sheet (such as Care Tracker) | Urine output if Foley catheter in use | | | | |
| | | Amount per 8 hour shift | | | |
| | | | <240 cc per 8 hour shift | | High |
| | | | ≥240-399 cc per 8 hour shift | | Medium |
| | | | ≥400-650 cc per 8 hour shift | | None |
| | | | >650 cc per 8 hour shift | | Medium |
| Electronic Flow Sheet | Wound assessment | | | | |
| | | Type of wound | | | |
| | | | pressure | | |
| | | | | No | None |
| | | | | Yes | Low |
| | | | Duration in days of any pressure ulcer | | |
| | | | | 0-1 days | High |
| | | | | 2-7 days | Medium |
| | | | | 8-30 days | Low |
| | | | | >30 days | None |
| | | | trauma | | |
| | | | Duration in days of any trauma wound | | |
| | | | | 0-1 days | High |
| | | | | 2-7 days | Medium |
| | | Odor of any wound | | | |
| | | | No | | None |
| | | | Yes | | Low |
| | | Support surface if truncal pressure ulcer is present ≥14 days | Standard mattress | | High |
| | | | Group 1 | | Low |
| | | | Group 2 | | None |
| Electronic flow sheet | If pressure ulcer is documented | Turning/repositioning program | | | |
| | | | Duration of days if not documented | | |
| | | | | None | High |
| | | | | 0-1 days | High |
| | | | | 2-7 days | Medium |
| | | | | 8-30 days | Low |
| | | | | >30 days | None |

-continued

| Source | Name | Description | Assessment | Severity/Flag | |
|---|---|---|---|---|---|
| Electronic Flow Sheet | POC glucose if ordered at least once per day | | | | Pattern Rules |
| | | No results recorded | | High | |
| | | 0-70 | | High | |
| | | 71-100 | | None | If 3 of 5 days, medium |
| | | 101-180 | | None | None |
| | | 181-300 | | None | If 5 of 7 days, medium |
| | | 301-400 | | None | If 5 of 7 days, high |
| | | ≥401 | | High | |
| MDS J0300 | Pain Presence | | No | None | |
| | | | Yes | None | If 3 of 5 days, medium |
| | | | Unable to answer | None | |
| MDS J0400 | Pain frequency | | 1. Almost constantly | High | |
| | | | 2. Frequently | Medium | |
| | | | 3. Occasionally | Low | |
| | | | 4. Rarely | None | |
| | | | 9. Unable to answer | None | |
| MDS J0600 | Pain intensity Numeric rating scale | | (00-10) | | |
| | | | 3-Jan | Low | |
| | | | 7-Apr | Medium | |
| | | | 10-Aug | High | |
| | Pain intensity Verbal Descriptor Scale | | 1. Mild. | Low | |
| | | | 2. Moderate. | Medium | If 5 of 7 days, high |
| | | | 3. Severe. | High | |
| | | | 4. Very severe, horrible. | High | |
| | | | 9. Unable to answer. | None | |

3. SNF Issues

| Source | Name | Description | Assessment | Severity/Flag |
|---|---|---|---|---|
| Electronic Flow Sheet (such as Care Tracker) | | | | |
| | Oral intake | | <25% | High |
| | | | 26-50% | Medium |
| | | | 51-75% | Low |
| | | | ≥76% | None |
| MDS E0100 | Behavior | hallucinations | | High |
| | | Delusions | | High |
| | | None | | None |
| MDS E0200 | Behavior | A. Physical behavioral symptoms directed toward others | 0. Behavior not exhibited. | None |
| | | | 1. Behavior of this type occurred 1 to 3 days. | Low |

-continued

| Source | Name | Description | Assessment | Severity/Flag |
|---|---|---|---|---|
| | | | 2. Behavior of this type occurred 4 to 6 days, but less than daily. | Medium |
| | | | 3. Behavior of this type occurred daily | High |
| | | B. Verbal behavioral symptoms directed toward others | 0. Behavior not exhibited. | None |
| | | | 1. Behavior of this type occurred 1 to 3 days. | Low |
| | | | 2. Behavior of this type occurred 4 to 6 days, but less than daily. | Medium |
| | | | 3. Behavior of this type occurred daily. | High |
| | | C. Other behavioral symptoms not directed toward others | 0. Behavior not exhibited. | None |
| | | | 1. Behavior of this type occurred 1 to 3 days. | Low |
| | | | 2. Behavior of this type occurred 4 to 6 days, but less than daily. | Medium |
| | | | 3. Behavior of this type occurred daily. | High |
| MDS C1310 | CAM | Is there evidence of an acute change in mental status from the resident's baseline? | | |
| | | | No | None |
| | | | Yes | High |
| | | Inattention | 0 Not present | None |
| | | | 1 continuously present | High |
| | | | 2 present but fluctuates | Medium |
| | | Disorganized thinking | 0 Not present | None |
| | | | 1 continuously present | High |
| | | | 2 present but fluctuates | Medium |
| | | Altered level of consciousness | 0 Not present | None |
| | | | 1 continuously present | High |
| | | | 2 present but fluctuates | Medium |
| MDS E0800 | Rejection of care - presence & frequency | | 0. Behavior not exhibited. | None |
| | | | 1. Behavior of this type occurred 1 to 3 days. | Low |
| | | | 2. Behavior of this type occurred 4 to 6 days, but less than daily. | Medium |
| | | | 3. Behavior of this type occurred daily. | High |

-continued

| Source | Name | Description | Assessment | Severity/Flag |
|---|---|---|---|---|
| MDS J1100 | Shortness of breath (dyspnea) | A. Shortness of breath or trouble breathing with exertion (e.g., walking, bathing, transferring). | | Low |
| | | B. Shortness of breath or trouble breathing when sitting at rest. | | Medium |
| | | C. Shortness of breath or trouble breathing when lying flat. | | High |
| | | Z. None of the above | | None |
| MDS O0700 | Physician orders | Over the last 14 days, on how many days did the physician (or authorized assistant or practitioner) change the resident's orders? | None | None |
| | | | 1-3 | Low |
| | | | 4-6 | Medium |
| | | | ≥7 | High |

4. SNF Laboratory Results

| Source | Name | Description | Assessment | Severity/Flag |
|---|---|---|---|---|
| Electronic Flow Sheet (such as Care Tracker) | | | | |
| | Oral intake | | <25% | High |
| | | | 26-50% | Medium |
| | | | 51-75% | Low |
| | | | ≥76% | None |
| MDS E0100 | Behavior | hallucinations | | High |
| | | Delusions | | High |
| | | None | | None |
| MDS E0200 | Behavior | A. Physical behavioral symptoms directed toward others | 0. Behavior not exhibited. | None |
| | | | 1. Behavior of this type occurred 1 to 3 days. | Low |
| | | | 2. Behavior of this type occurred 4 to 6 days, but less than daily. | Medium |
| | | | 3. Behavior of this type occurred daily | High |
| | | B. Verbal behavioral symptoms directed toward others | 0. Behavior not exhibited. | None |
| | | | 1. Behavior of this type occurred 1 to 3 days. | Low |
| | | | 2. Behavior of this type occurred 4 to 6 days, but less than daily. | Medium |
| | | | 3. Behavior of this type occurred daily. | High |

-continued

| Source | Name | Description | Assessment | Severity/Flag |
|---|---|---|---|---|
| | | C. Other behavioral symptoms not directed toward others | 0. Behavior not exhibited. | None |
| | | | 1. Behavior of this type occurred 1 to 3 days. | Low |
| | | | 2. Behavior of this type occurred 4 to 6 days, but less than daily. | Medium |
| | | | 3. Behavior of this type occurred daily. | High |
| MDS C1310 | CAM | Is there evidence of an acute change in mental status from the resident's baseline? | | |
| | | | No | None |
| | | | Yes | High |
| | | Inattention | 0 Not present | None |
| | | | 1 continuously present | High |
| | | | 2 present but fluctuates | Medium |
| | | Disorganized thinking | 0 Not present | None |
| | | | 1 continuously present | High |
| | | | 2 present but fluctuates | Medium |
| | | Altered level of consciousness | 0 Not present | None |
| | | | 1 continuously present | High |
| | | | 2 present but fluctuates | Medium |
| MDS E0800 | Rejection of care - presence & frequency | | 0. Behavior not exhibited. | None |
| | | | 1. Behavior of this type occurred 1 to 3 days. | Low |
| | | | 2. Behavior of this type occurred 4 to 6 days, but less than daily. | Medium |
| | | | 3. Behavior of this type occurred daily. | High |
| MDS J1100 | Shortness of breath (dyspnea) | A. Shortness of breath or trouble breathing with exertion (e.g., walking, bathing, transferring). | | Low |
| | | B. Shortness of breath or trouble breathing when sitting at rest. | | Medium |
| | | C. Shortness of breath or trouble breathing when lying flat. | | High |
| | | Z. None of the above | | None |

| Source | Name | Description | Assessment | Severity/Flag |
|---|---|---|---|---|
| MDS O0700 | Physician orders | Over the last 14 days, on how many days did the physician (or authorized assistant or practitioner) change the resident's orders? | None | None |
| | | | 1-3 | Low |
| | | | 4-6 | Medium |
| | | | ≥7 | High |

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system configured to facilitate computer-assisted care for skilled nursing facility (SNF) patients at risk of clinical deterioration and/or in need of medical intervention relative to a larger population of SNF patients, the system comprising:
one or more hardware processors configured by machine-readable instructions to:
obtain care information for the larger population of SNF patients, the care information comprising physiological information collected by caregivers during care for the larger population of SNF patients;
facilitate collection of SNF enhancement information for the larger population of SNF patients, the SNF enhancement information comprising information related to SNF specific care provided to the larger population of SNF patients;
determine care information scores for individual SNF patients based on the obtained care information, the care information scores determined using a first set of severity weights associated with individual components of the care information;
determine SNF enhancement scores for the individual SNF patients based on the SNF enhancement information, the SNF enhancement scores determined using a second set of severity weights associated with individual components of the SNF enhancement information, wherein the second set of severity weights are heavier than the first set of severity weights such that the SNF enhancement scores are weighted more heavily than the care information scores for the individual SNF patients;
combine the care information scores with the SNF enhancement scores for the individual SNF patients to determine a combined score that indicates risk of clinical deterioration and/or a need for medical intervention for the individual SNF patients;
control a medical device associated with the individual SNF patients to treat each individual SNF patient based on the combined score for the respective individual patient; and
one or more computing devices configured to:
display the combined scores for the individual SNF patients as a triaged list of individual SNF patients in a first view of a graphical user interface displayed on the one or more computing devices,
display of one or more fields in a second view of the graphical user interface configured to receive entry and/or selection of the SNF enhancement information, and
provide instructions to caregivers via a third view of the graphical user interface.

2. The system of claim 1, wherein the SNF enhancement information comprises information related to one or more of fluid intake and/or output from, bowel movements of, oral food intake of, behavior of, wound assessment and/or treatment of, blood glucose of, therapy received by, or a level of physical assistance received by, individual SNF patients.

3. The system of claim 1, wherein the SNF enhancement information comprises information recorded in one or more flow sheets associated with a SNF.

4. The system of claim 1, wherein the weighted individual components of the care information comprise care measurements, observed care issues, care surveys, discharge information, and readmission information.

5. The system of claim 1, wherein the weighted individual components of the SNF enhancement information comprise SNF surveys, SNF measurements, SNF issues, and SNF lab results.

6. The system of claim 1, further comprising:
one or more sensors configured to generate output signals conveying information included in the care information and/or the SNF enhancement information.

7. A method for facilitating computer-assisted care for skilled nursing facility (SNF) patients at risk of clinical deterioration and/or in need of medical intervention relative to a larger population of SNF patients, the system comprising one or more hardware processors and one or more computing devices, the method comprising:

obtaining, with the one or more hardware processors, care information for the larger population of SNF patients, the care information comprising physiological information collected by caregivers during care for the larger population of SNF patients;

facilitating, with the one or more hardware processors, collection of SNF enhancement information for the larger population of SNF patients, the SNF enhancement information comprising information related to SNF specific care provided to the larger population of SNF patients;

determining, with the one or more hardware processors, care information scores for individual SNF patients based on the obtained care information, the care information scores determined using a first set of severity weights associated with individual components of the care information;

determining, with the one or more hardware processors, SNF enhancement scores for the individual SNF patients based on the SNF enhancement information, the SNF enhancement scores determined using a second set of severity weights associated with individual components of the SNF enhancement information, wherein the second set of severity weights are heavier than the first set of severity weights such that the SNF enhancement scores are weighted more heavily than the care information scores for the individual SNF patients;

combining, with the one or more hardware processors, the care information scores with the SNF enhancement scores for the individual SNF patients to determine a combined score that indicates risk of clinical deterioration and/or a need for medical intervention for the individual SNF patients;

controlling, with the one or more hardware processors, a medical device associated with an individual SNF patient to treat the individual SNF patient based on the combined score for the individual patient;

displaying, with the one or more computing devices, the combined scores for the individual SNF patients as a triaged list of individual SNF patients in a first view of a graphical user interface displayed on the one or more computing devices;

displaying one or more fields in a second view of the graphical user interface configured to receive entry and/or selection of the SNF enhancement information; and displaying instructions to a caregiver via a third view of the graphical user interface.

8. The method of claim 7, wherein the SNF enhancement information comprises information related to one or more of fluid intake and/or output from, bowel movements of, oral food intake of, behavior of, wound assessment and/or treatment of, blood glucose of, therapy received by, or a level of physical assistance received by, individual SNF patients.

9. The method of claim 7, wherein the SNF enhancement information comprises information recorded in one or more flow sheets associated with a SNF.

10. The method of claim 7, wherein the weighted individual components of the care information comprise care measurements, observed care issues, care surveys, discharge information, and readmission information.

11. The method of claim 7, wherein the weighted individual components of the SNF enhancement information comprise SNF surveys, SNF measurements, SNF issues, and SNF lab results.

12. The method of claim 7, wherein the system further comprises one or more sensors, the method further comprising:

generating, with the one or more sensors, output signals conveying information included in the care information and/or the SNF enhancement information.

13. A non-transitory medium for facilitating computer-assisted care for skilled nursing facility (SNF) patients at risk of clinical deterioration and/or in need of medical intervention relative to a larger population of SNF patients when instructions on the non-transitory medium are executed by a computer, the non-transitory medium comprising:

instructions for obtaining care information for the larger population of SNF patients, the care information comprising physiological information collected by caregivers during care for the larger population of SNF patients;

instructions for facilitating collection of SNF enhancement information for the larger population of SNF patients, the SNF enhancement information comprising information related to SNF specific care provided to the larger population of SNF patients;

instructions for determining care information scores for individual SNF patients based on the obtained care information, the care information scores determined using a first set of severity weights associated with individual components of the care information;

instructions for determining SNF enhancement scores for the individual SNF patients based on the SNF enhancement information, the SNF enhancement scores determined using a second set of severity weights associated with individual components of the SNF enhancement information, wherein the second set of severity weights are heavier than the first set of severity weights such that the SNF enhancement scores are weighted more heavily than the care information scores for the individual SNF patients;

instructions for combining the care information scores with the SNF enhancement scores for the individual SNF patients to determine a combined score that indicates risk of clinical deterioration and/or a need for medical intervention for the individual SNF patients;

instructions for controlling, with the one or more hardware processors, a medical device associated with an individual SNF patient to treat the individual SNF patient based on the combined score for the individual patient;

instructions for displaying the combined scores for the individual SNF patients as a triaged list of individual SNF patients in a first view of a graphical user interface;

instructions for displaying one or more fields in a second view of the graphical user interface configured to receive entry and/or selection of the SNF enhancement information; and instructions for displaying instructions to a caregiver via a third view of the graphical user interface.

14. The non-transitory medium of claim 13, wherein the SNF enhancement information comprises information related to one or more of fluid intake and/or output from, bowel movements of, oral food intake of, behavior of, wound assessment and/or treatment of, blood glucose of, therapy received by, or a level of physical assistance received by, individual SNF patients.

15. The non-transitory medium of claim 13, wherein the SNF enhancement information comprises information recorded in one or more flow sheets associated with a SNF.

16. The non-transitory medium of claim 13, wherein the weighted individual components of the care information comprise care measurements, observed care issues, care surveys, discharge information, and readmission information.

17. The non-transitory medium of claim 13, wherein the weighted individual components of the SNF enhancement information comprise SNF surveys, SNF measurements, SNF issues, and SNF lab results.

18. The non-transitory medium of claim 13, wherein the system further comprises:
   instructions for generating output signals conveying information included in the care information and/or the SNF enhancement information.

* * * * *